(12) United States Patent
Cruz

(10) Patent No.: US 6,802,714 B2
(45) Date of Patent: Oct. 12, 2004

(54) DENTAL AESTHETIC GUIDE

(76) Inventor: Gerald M. Cruz, 35251 34th Ave. S., Auburn, WA (US) 98001

( * ) Notice: Subject to any disclaimer, the term of this patent is extended or adjusted under 35 U.S.C. 154(b) by 135 days.

(21) Appl. No.: 10/177,033

(22) Filed: Jun. 21, 2002

(65) Prior Publication Data
US 2003/0235799 A1 Dec. 25, 2003

(51) Int. Cl.⁷ .............................................. A61C 19/10
(52) U.S. Cl. ...................................................... 433/26
(58) Field of Search ................................ 433/26, 203.1

(56) References Cited

U.S. PATENT DOCUMENTS

| | | | | |
|---|---|---|---|---|
| 4,657,399 A | * | 4/1987 | Hall | ............................ 356/421 |
| 4,919,617 A | * | 4/1990 | Antons et al. | ................. 433/26 |
| 5,078,598 A | * | 1/1992 | Neisse | ........................... 433/26 |
| 5,240,414 A | | 8/1993 | Thompson | |
| 5,261,815 A | | 11/1993 | Pozzi | |
| 5,482,459 A | | 1/1996 | Yarovesky | |
| 5,498,157 A | * | 3/1996 | Hall | ............................. 433/26 |
| 5,529,492 A | | 6/1996 | Yarovesky | |
| 5,588,834 A | | 12/1996 | Resk | |
| 5,624,262 A | | 4/1997 | Yarovesky | |
| 5,685,712 A | | 11/1997 | Fischer | |
| 5,692,900 A | | 12/1997 | Fischer | |
| 6,030,209 A | * | 2/2000 | Panzera et al. | ................ 433/26 |
| 6,328,563 B1 | * | 12/2001 | Hobo | .......................... 433/26 |

* cited by examiner

Primary Examiner—Ralph A. Lewis
(74) Attorney, Agent, or Firm—David L. Tingey

(57) ABSTRACT

A tooth characterization guide includes several sets of tooth samples, each set representing a tooth different characteristic. The guide allows a dentist to compare guide samples in value and translucency with a patient's teeth to obtain an accurate characterization of a tooth prosthesis for the patient. From these tooth samples the dentist is able to first choose a suitable translucency, which is the most important and influential factor for true tooth replication from a first set of samples. The dentist then is able to choose a suitable brightness from a second set of samples. The dentist then is able to choose a suitable color and saturation from a third set of samples. The dental laboratory utilizing the guide selections can then objectively reproduce the observed tooth appearance.

16 Claims, 5 Drawing Sheets

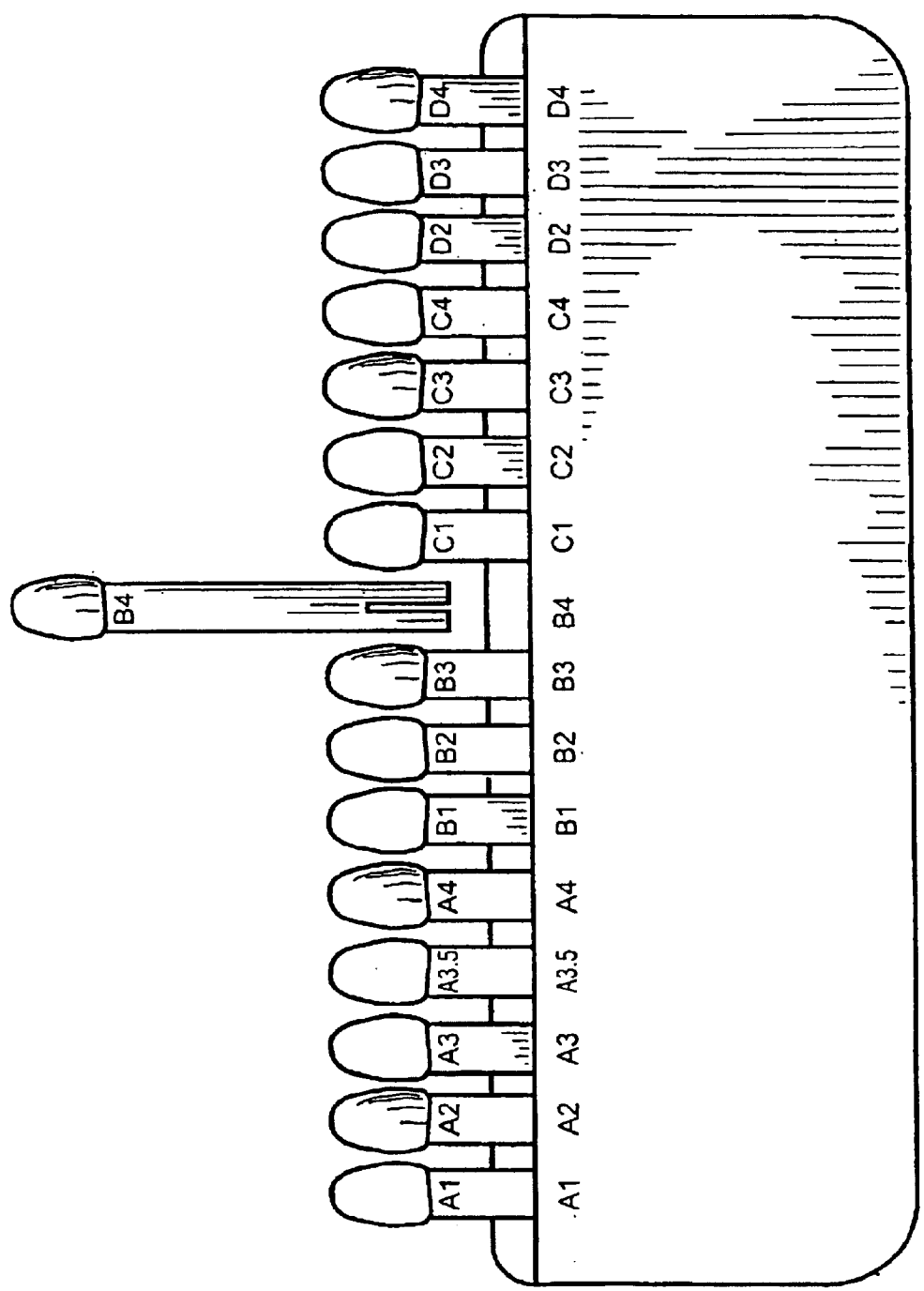
FIG. 2 [PRIOR ART]

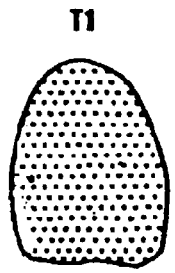
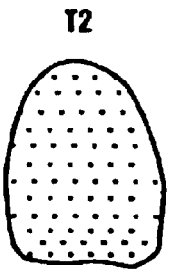
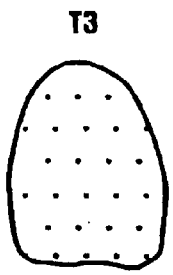
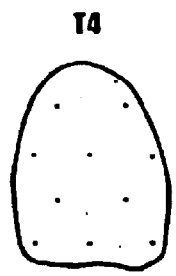
FIG. 3A — EFFECT (T1)
FIG. 3B — OPACEOUS DENTIN (T2)
FIG. 3C — DENTIN (T3)
FIG. 3D — ENAMEL (T4)
FIG. 3E — CLEAR (T5)
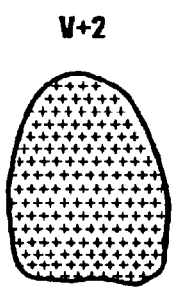
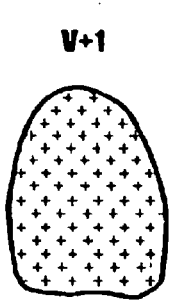
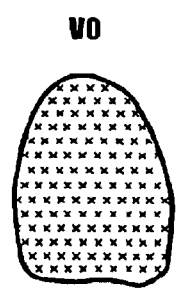
FIG. 4A — BLEACH 2 (V+2)
FIG. 4B — BLEACH 1 (V+1)
FIG. 4C — NEUTRAL (V0)
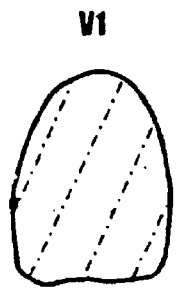
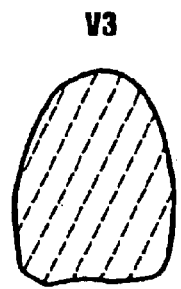
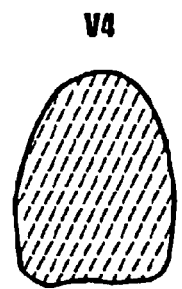
FIG. 4D — NORMAL 1 (V1)
FIG. 4E — NORMAL 2 (V2)
FIG. 4F — NORMAL 3 (V3)
FIG. 4G — NORMAL 4 (V4)
FIG. 4H — NORMAL 5 (V5)

HUE A
CHROMA 1

HUE A
CHROMA 2

HUE A
CHROMA 3

HUE A
CHROMA 3.5

HUE A
CHROMA 4

HUE B
CHROMA 1

HUE B
CHROMA 2

HUE B
CHROMA 3

HUE B
CHROMA 4

HUE C
CHROMA 1

HUE C
CHROMA 2

HUE C
CHROMA 3

HUE C
CHROMA 4

HUE D
CHROMA 1

HUE D
CHROMA 2

HUE D
CHROMA 3

( FIGS. 5A - 5P )

DENTAL AESTHETIC GUIDE

BACKGROUND

1. Field of the Invention

This invention relates to dental reconstruction and more specifically to methods and guides to describe aesthetic components of natural teeth with multidimensional descriptors representing aesthetic features of a tooth useful in reconstructive dentistry.

2. Prior Art

It is common for manufacturers of tooth prostheses to provide samples of multi-colored fabricated teeth as a shade guide for comparison with a patient's teeth to determine tooth color shade and color saturation. The dentist then communicates that color shade and saturation to a dental laboratory and the dental laboratory creates a tooth as described. Unfortunately, the new replacement tooth or crown often does not match the patients mouth, frustrating the patient, the dentist, and the laboratory technician. Perhaps the most frustrating and disappointing element in tooth reconstruction is a restoration that doesn't blend with surrounding natural teeth. With advances in ceramic technology, disappointing results are not for lack of capability to reproduce teeth but more so in the approach to measuring and communicating tooth appearance between an observer, typically in a dental office, and a reconstructive technician, typically in a dental laboratory.

For the past fifty years or so the standard communication for the appearance of tooth structure has been color. Hue describes the general color group of a tooth, a characteristic established at birth. Chroma is the saturation of color within that hue color group. Dental offices have attempted to describe a tooth to a dental laboratory by referring to a standard tab in a shade guide, comparing a tooth to those in the guide to locate the most similar hue and saturation. Hue and chroma have been represented in tab form from the shade guide to represent first the correct color group (hue) and then the proper amount of color saturation (chroma). Certainly color and hue are important components to tooth description, but alone they are not adequate. There are additional and important tooth characteristics that also require communication to the reconstructive technician. Additional variables are required, including optical density and brightness. Optical Density means the translucency of the tooth, the degree light is reflected or transmitted. Value is the brightness of the tooth.

About ten years ago, some technicians began including value as a second element of tooth description. By adding value as a descriptor, a tooth could be described not only as having a certain color and amount of color within a color shade, but it could also be described by how bright the tooth was. By simply adding a value rating to a tooth prescription, one gains good predictability about how the final crown will appear. Value is, in fact, as important as hue and chroma when one wants a crown to disappear and blend in.

Though hue and color have been the traditional descriptors for many years, and recently value, or brightness, has been added by some dental professionals, perhaps the most important factor in dental ceramics is optical density, or translucency—the passage of light through different parts of a crown. It is now recognized that the most visibly offensive restorations fail to display the depth, translucency and vitality of natural teeth. Crowns that ignore translucency don't blend in with the surrounding dentition; they attract too much attention in all lighting conditions irrespective of color group or saturation. One might consider two teeth displaying the same hue and chroma and the same value or brightness, yet one may have a very chaulky appearance and the other may have a very glassy look. To describe these two teeth with the use of only value and hue and chroma is nearly impossible; they would have the same prescription. The defining visual difference is translucency, the ability of a tooth to transmit light, which can be independent of value and also independent of chroma and hue. Optical density must be utilized to allow a description of a glassy or chalky tooth and must be recognized as an additional dimension in the description of the visual appearance of teeth.

The significant advances in dental porcelain have been the changes in the optical qualities of the material. One of the first optical improvements was fluorescence. Ultraviolet light interacts with materials causing them to fluoresce and emit a bright, visible whitish light. The inclusion of fluorescent material in dental porcelain enabled it to brighten in sunlight and UV light conditions similar to natural teeth, eliminating noticeable value changes.

Another advance in ceramics has been opalescence, an optical property that controls the passage of light by the size of its wavelength. Microfine particles are incorporated into porcelain to scatter and reflect blue wavelengths in direct light and allow longer orange wavelengths to pass through in indirect lighting conditions. Hydroxyapatite crystals in natural teeth are similar size (0.02 to 0.04 microns) and give teeth natural opalescence.

Opalescence in teeth is especially visible in the anterior region. Anteriors can be subject to both direct and indirect lighting as opposed to posteriors that we view in direct light only. As a result, this opal affect is primarily used in incisal or enamel powders.

Although the bluish and orange effects contribute to the realism of a restoration, the more practical advantage of opal incisal is the control of brightness. Before opalescence was introduced into dental porcelain, increased translucency meant increased grayness and lower value. Opalescing particles raise the refractive index of light due to their interaction with light, both by scattering and reflecting light waves. This higher refractive index allows the laboratory to produce a bright, beautiful translucency that will not gray in the oral environment.

This advancement was the key to controlling value and translucency independently. Using a complex selection of body porcelain, incisals, and modifiers several levels of opacity or translucency can be constructed. Layering these porcelains in different combination controls passage of light even in different parts of a crown as necessary to correctly reproduce an original tooth, blocking the passage of light by reflecting it or selectively scattering and diffusing it or alternately allowing it to pass and transmit through the structure, producing an appearance of a natural tooth.

With the recognition that in order to adequately describe a tooth, translucency and value must be described in addition to hue and chroma. What is needed now is a process of simply and logically communicating characteristics of a natural tooth between a dental office and a dental laboratory, a method coordinated to the changes in modern dental porcelain systems yet familiar to the dental office and inexpensive so dental offices will be inclined to readily incorporate the process.

These objects are achieved in a dental aesthetic guide that incorporates these several descriptors of translucency, brightness, hue and chroma to represent a patient's appearance.

SUMMARY OF THE INVENTION

A tooth characterization guide allows a dentist to compare additional guide samples in value and translucency with a patient's mouth in the method similar to that previously used by dentists in obtaining hue and chroma of a tooth. From these tooth samples the dentist is able to first choose a suitable translucency, which is the most important and influential factor for true tooth replication from a first set of samples. The dentist then is able to choose a suitable brightness from a second set of samples. The dentist then is able to choose a suitable color and saturation from a third set of samples. Typically, the dentist is able to use his set of samples of hue and chroma that he is already familiar with using. If desired, additional anterior tooth characteristics may also be selected, including a cracking, check lines, spotting, banding, staining, white hallo and orange hallo.

BRIEF DESCRIPTION OF THE DRAWINGS

FIG. 2 is a rack showing removable samples of tooth hue within hue groups A through D with chroma samples within each hue group, denoted A1 and A4 within A group, B1 through B4 within B group, C1 through C4 within C group, D1 through D4 within D group.

FIGS. 3A–3E are front elevational views of a set of tooth samples showing a range of translucency.

FIGS. 4A–4H are front elevational views of a set of tooth samples showing a range of value, or brightness.

DETAILED DESCRIPTION OF THE PREFERRED EMBODIMENT

Figure 1:
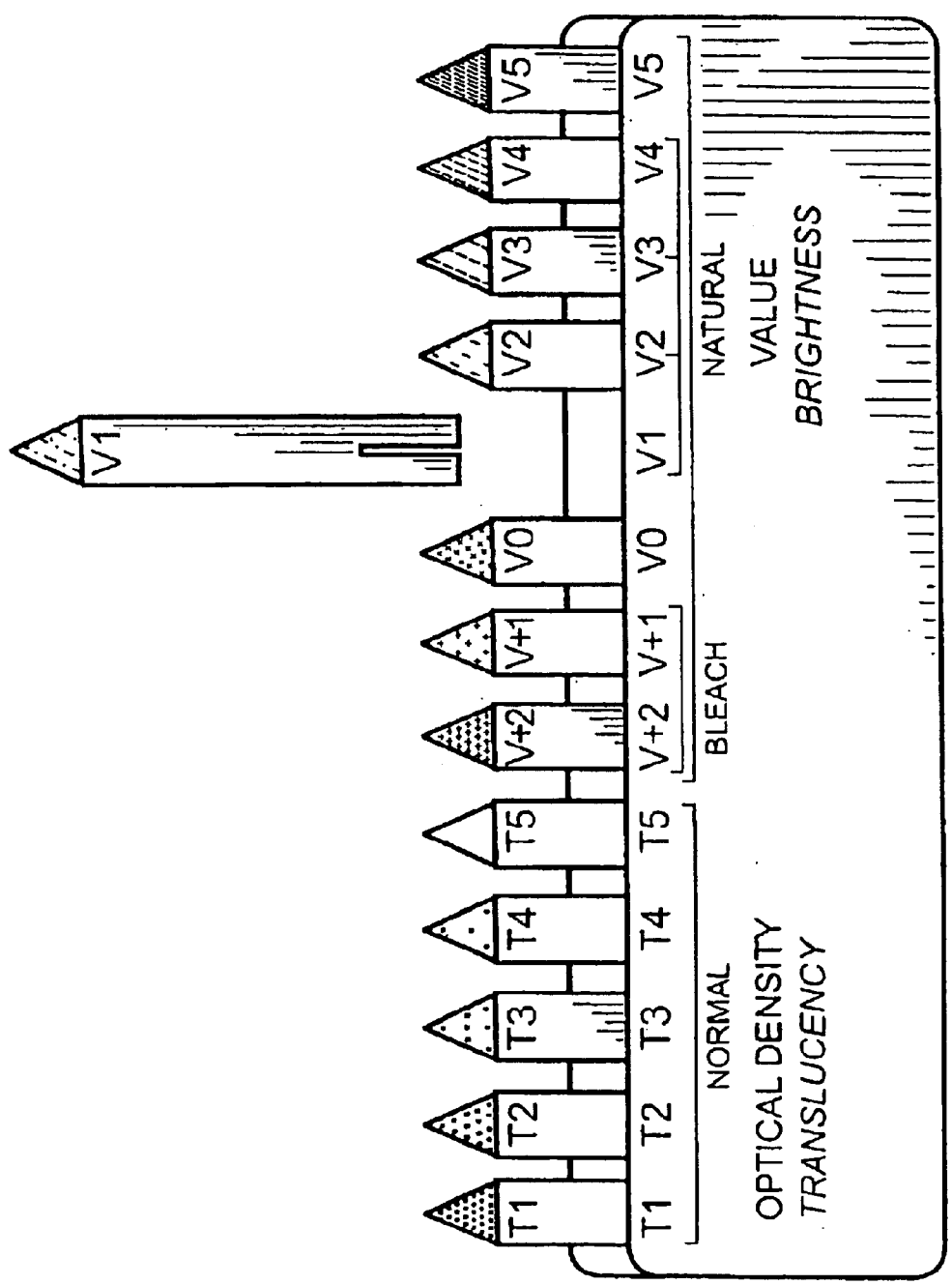
FIG. 1 is a rack showing removable samples of tooth translucency denoted as T1 through T5 and removable samples of tooth brightness denoted as V+2 through V5.
Figure 5A:
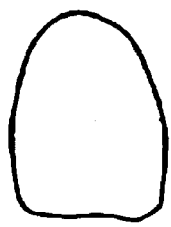
FIGS. 5A–5P are front elevational views of a set of tooth samples showing a range of hue and chroma.
Figure 5B:
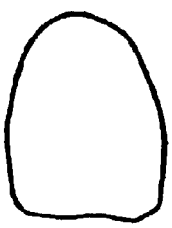
Figure 5C:
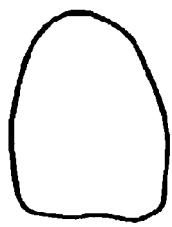
Figure 5D:
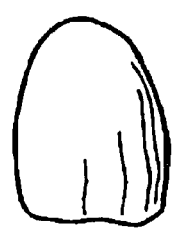
Figure 5E:
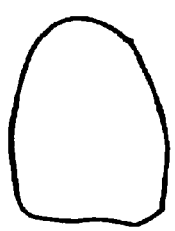
Figure 5F:
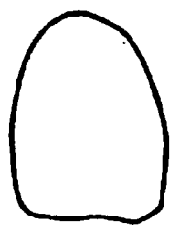
Figure 5G:
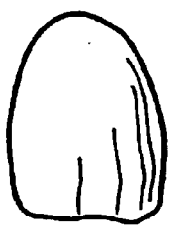
Figure 5H:
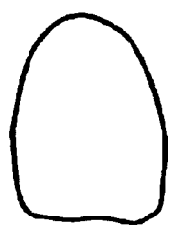
Figure 5I:
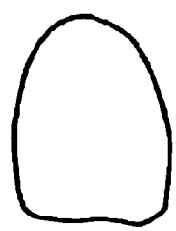
Figure 5J:
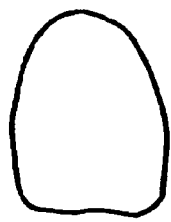
Figure 5K:
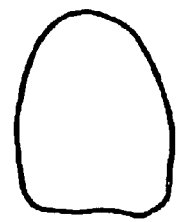
Figure 5L:
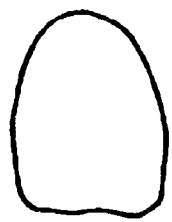
Figure 5M:
Figure 5N:
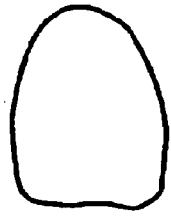
Figure 5O:
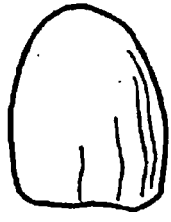
Figure 5P:
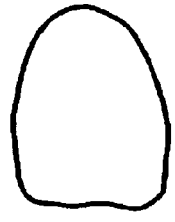
Figure 6:
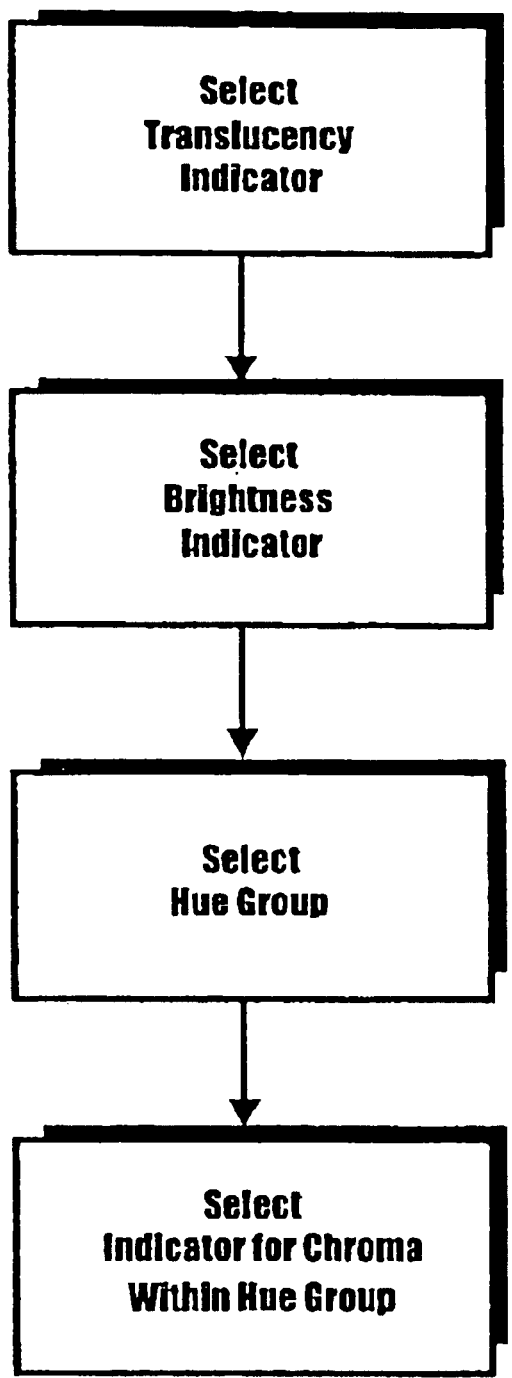
FIG. 6 is a flow chart illustrating the steps of the method of selecting characterizations for a tooth prosthesis.

The present invention is a visual guide that aids in more accurately describing aesthetic features of a tooth. The guide provides a structure that enables a dental office to communicate tooth appearance in a three-dimensional vector that more accurately describes a tooth to the dental laboratory than has been previously done using only color features. The subjective nature of the selection process is eliminated when the dental office and the laboratory utilize the same standards.

Additional two dimensions of transparency and value are added to the color features of hue and chroma. A first set of samples represents a range of tooth translucency. A second set of samples represents a range of tooth brightness. A third set of samples represents a range of hue and chroma. This third set can be those already used within the dental office that are available from commercial manufacturers.

Any number of tabs can be employed in each of the descriptor dimensions. It has been experimentally determined that a range using eight samples adequately describes brightness and five samples adequately represent translucency, or optical density. Because each descriptor is mostly independent of the other descriptor dimensions, it is not necessary to have a different set of density tabs for each color group because optical density generally is not a function of color. Nor is value a function of color or optical density. Therefore an adequate assembly of tabs includes five translucency tabs representing the range observed in natural teeth, and eight brightness tabs representing natural brightness and bleached teeth together with a commercially available set of color tabs, such as is available from Vita which provides sixteen tabs, each having effective the same translucency.

Because optical density and value have a stronger influence on the appearance of a tooth than does color, they are typically selected first. A value or brightness is determined by comparison with one of the eight value tabs after optical density is selected by comparison with the five translucency tabs. Then a color group is selected and a color saturation level is selected within the color group to represent hue and chroma values.

Having described the invention, what is claimed is as follows:

1. A tooth characterization guide adapted to match samples to aesthetic qualities of a natural tooth independently in translucency, brightness, and hue and chroma for construction of a matching tooth prosthesis, comprising:
   means for selecting a translucency for the tooth prosthesis from a first guide portion,
   means for selecting a brightness for the tooth prosthesis from a second guide portion independently from the first guide portion, and
   means for selecting a hue and chroma for the tooth prosthesis from a third guide portion independently from the first and second guide portions.

2. The tooth characterization guide of claim 1, wherein the means for selecting a translucency for the tooth prosthesis from a first guide portion includes a first set of a plurality of samples each with a different translucency suitable in range of translucency of natural teeth for selection of a translucency sample closest in translucency to a natural tooth against which it can be compared.

3. The tooth characterization guide of claim 1, wherein the means for selecting a brightness for the tooth prosthesis from a second guide portion includes a second set a plurality of samples each with a different brightness suitable in range of a brightness of natural teeth for selection of a different brightness sample closest in brightness to a natural tooth against which it can be compared.

4. The tooth characterization guide of claim 1, wherein the means for selecting a hue and chroma for the tooth prosthesis from a third guide portion includes a third set a plurality of samples each with a different hue and chroma suitable in range of a brightness of natural teeth for selection of a different hue and chroma sample closest in hue and chroma to a natural tooth against which it can be compared.

5. The tooth characterization guide of claim 2 wherein said plurality of samples each with a different translucency has the same effective brightness.

6. The tooth characterization guide of claim 2 wherein said plurality of samples each with a different translucency has the same effective hue and chroma.

7. The tooth characterization guide of claim 3 wherein said plurality of samples each with a different brightness has the same effective translucency.

8. The tooth characterization guide of claim 3 wherein said plurality of samples each with a different brightness has the same effective hue and chroma.

9. The tooth characterization guide of claim 4 wherein said plurality of samples each with a different hue and chroma has the same effective translucency.

10. The tooth characterization guide of claim 4 wherein said plurality of samples each with a different hue and chroma has the same effective brightness.

11. A tooth characterization guide adapted to match samples to aesthetic qualities of a natural tooth independently in translucency, brightness, and hue and chroma for construction of a matching tooth prosthesis, comprising:

a first set of a plurality of first samples comprising a first guide portion, each of said first samples having a different translucency suitable in range of translucency of natural teeth for selection of a translucency sample closest in translucency to a natural tooth against which it can be compared for selecting a translucency for the tooth prosthesis from a first guide portion, a second set of a plurality of second samples comprising a second guide portion, each of said second samples having a different brightness suitable in range of a brightness of natural teeth for selection of a different brightness sample closest in brightness to a natural tooth against which it can be compared for selecting a brightness for the tooth prosthesis from a second guide portion, a third set of a plurality of third samples each comprising a second guide portion each of said third samples having a different hue and chroma suitable in range of a brightness of natural teeth for selection of a different hue and chroma sample closest in hue and chroma to a natural tooth against which it can be compared for selecting a hue and chroma for the tooth prosthesis from a third guide portion.

12. The tooth characterization guide of claim 11 wherein said plurality of first samples has the same effective brightness and the same effective hue and chroma.

13. The tooth characterization guide of claim 11 wherein said plurality of second samples has the same effective translucency and the same effective hue and chroma.

14. The tooth characterization guide of claim 11 wherein said plurality of third samples has the same effective brightness and the same effective translucency.

15. A method of characterizing a tooth for the construction of a tooth prosthesis, comprising the steps of:

(a) selecting a translucency sample for the tooth prosthesis from a first set of samples, wherein said first set includes a plurality of first samples each having a different translucency;

(b) selecting a brightness indicator for the tooth prosthesis from a second set of tooth samples independently from and without regard to the first set of samples, wherein said second set includes a plurality of samples having different brightness;

(c) selecting a hue and chroma indicator for the tooth prosthesis from a third set of samples independently from and without regard to the first and second sets of samples, wherein said third set includes a plurality of samples having different hue and chroma.

16. The method of claim 15 wherein step (c) includes the step of selecting a general color group within hue samples followed by the step of selecting a chroma sample within the selected color group.

* * * * *